(12) United States Patent
Nolan et al.

(10) Patent No.: US 6,326,157 B1
(45) Date of Patent: Dec. 4, 2001

(54) RECOMBINANT FLUORESCENT PROTEIN MICROSPHERE CALIBRATION STANDARD

(75) Inventors: John P. Nolan; Rhiannon L. Nolan, both of Santa Fe; Teresa Ruscetti; Bruce E. Lehnert, both of Los Alamos, all of NM (US)

(73) Assignee: The Regents of the University of California

(*) Notice: Subject to any disclaimer, the term of this patent is extended or adjusted under 35 U.S.C. 154(b) by 0 days.

(21) Appl. No.: 09/264,544

(22) Filed: Mar. 5, 1999

Related U.S. Application Data

(60) Provisional application No. 60/076,981, filed on Mar. 5, 1998.

(51) Int. Cl.[7] .............................. G01N 33/53; C12Q 1/66
(52) U.S. Cl. .................................. 435/7.1; 435/8; 435/15; 435/7.5
(58) Field of Search .................................. 435/7.1, 7.5, 8, 435/68.1, 69.1, 69.7, 7.92, 7.95

(56) References Cited

U.S. PATENT DOCUMENTS

| | | | |
|---|---|---|---|
| 5,545,551 | * | 8/1996 | Johnson et al. .................... 435/252.3 |
| 5,723,218 | * | 3/1998 | Haugland et al. ................... 428/402 |
| 5,723,584 | * | 3/1998 | Schatz .................... 530/408 |

OTHER PUBLICATIONS

Patterson et al. (Nov. 1997) Biophys. J. Vol. 73, pp. 2782–2790.*
Oker–Blom et al. (1996) FEBS Letters 389, pp. 238–243.*
Cronan (1990) J. Biol. Chem. 265/18, pp. 10327–10333.*
Mitchell et al. (1995) FEBS Letters 368, pp. 148–150.*
Vogt et al. (1989) Cytometry, 10, pp. 294–302.*
George H. Patterson et al., "Use of the Green Fluorescent Protein and its Mutants in Quantitative Fluorescence Microscopy," Biophysical Journal 73, 2782 (1997).
Martin Chalfie et al., "Green Fluorescent Protein as a Marker for Gene Expression," Science 263, 802 (1994).
A. Schwartz et al., "Standardizing Flow Cytometry: Construction of a Standardized Fluorescence Calibration Plot Using Matching Spectral Calibrators," Cytometry 26, 22 (1996).
Robert F. Vogt, "Model System Evaluating Fluorescein–Labeled Microbeads as Internet Standards to Calibrate Fluorescence Intensity on Flow Cytometers," Cytometry 10, 294 (1989).
Avidin–Biotin Technology, (Eds. Meir Wilchek and Edward A. Bayer, Academic Press, Inc. (1990), in vol. 184 of Methods in Enzymology.
John E. Cronan, Jr., "Biotination of Proteins in vivo," J. Biolog. Chem. 265, 10327 (1990).
J. T. Murphy and J. C. Lagarias, "The Phytoflkuors: A New Class of Fluorescent Protein Probes," Current Biology 7, 870 (1997).

* cited by examiner

Primary Examiner—Karen Cochrane Carlson
(74) Attorney, Agent, or Firm—Samuel M. Freund

(57) ABSTRACT

A method for making recombinant fluorescent protein standard particles for calibration of fluorescence instruments.

10 Claims, 3 Drawing Sheets

RECOMBINANT FLUORESCENT PROTEIN MICROSPHERE CALIBRATION STANDARD

CROSS REFERENCE TO RELATED APPLICATIONS

The present patent application claims the benefit of Provisional Patent Application No. 60/076,981 which was filed on Mar. 05, 1998.

FIELD OF THE INVENTION

The present invention relates generally to the use of recombinant fluorescent: proteins as markers for gene expression and as fluorescent fusion protein tags and, more specifically, to the preparation of green fluorescent protein microsphere standards. This invention was made with government support under Contract No. W-7405-ENG-36 awarded by the U.S. Department of Energy. The government has certain rights in the invention.

BACKGROUND OF THE INVENTION

The *Aequorea victoria* green fluorescent protein's (GFP) rising popularity in recent years can be attributed to its utility as both a nontoxic marker for gene expression and as a fluorescent fusion protein tag, primarily for use with fluorescence microscopy (FM) or flow cytometry (FC). To date, these methods have been used to provide qualitative information on a tagged gene product's expression level and/or cell locale.

With the growing use of GFP for studies of gene expression, and with the development of brighter, wavelength-shifted mutant GFPs which have enabled the tailoring of its standard use to conventional flow cytometry and fluorescence microscopy lasers and/or filter sets, it has become important to develop procedures for quantitative GFP analysis in flow cytometers. See, e.g., "Use of the Green Fluorescent Protein and its Mutants in Quantitative Fluorescence Microscopy," by George H. Patterson et al., Biophysical Journal 73, 2782 (1997), which discusses the spectroscopy of GFP in bulk samples, and "Green Fluorescent Protein as a Marker for Gene Expression," by Martin Chalfie et al., Science 263, 802 (1994). The difficulty of attaching GFP to microspheres has prevented GFP standards for flow cytometry from being developed.

Relatively small fluorophores such as fluorescein isothiocyanate have been attached to microbeads and used as calibration standards for flow cytometry. See, e.g., "Standardizing Flow Cytometry: Construction of a Standardized Fluorescence Calibration Plot Using Matching Spectral Calibrators" by A. Schwartz et al., Cytometry 26, 22 (1996), and "Model System Evaluating Fluorescein-Labeled Microbeads as Internal Standards to Calibrate Fluorescence Intensity on Flow Cytometers," by Robert F. Vogt, Jr. et al., Cytometry 10, 294 (1989).

It is well known that biotin and the egg-white protein avidin (or streptavidin, its bacterial relative from Streptomyces avidinii), form a complex having a very large affinity ($K_a=10^{15}$ $M^{-1}$). This interaction is so strong that even biotin coupled to proteins is available for binding by avidin. See, e.g., *Avidin-Biotin Technology*, (Eds. Meir Wilchek and Edward A. Bayer, Academic Press, Inc. (1990)), in Volume 184 of *Methods in Enzymology*.

Accordingly, it is an object of the present invention to produce recombinants fluorescent protein microsphere calibration standards.

Another object of the present invention is to produce green fluorescent protein microsphere calibration standards.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for the preparation of recombinant fluorescent protein standard microspheres hereof may comprise in combination: fusing an affinity tag with the recombinant fluorescent protein; and attaching the affinity tag to a binding partner incorporated onto the microspheres, whereby the recombinant fluorescent protein is affixed to the microspheres.

Preferably, the recombinant fluorescent protein is enhanced green fluorescent protein, the affinity tag is biotin, and the binding partner is avidin or streptavidin.

It is also preferred that the microspheres are avidin or streptavidin microspheres.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Figure 1:
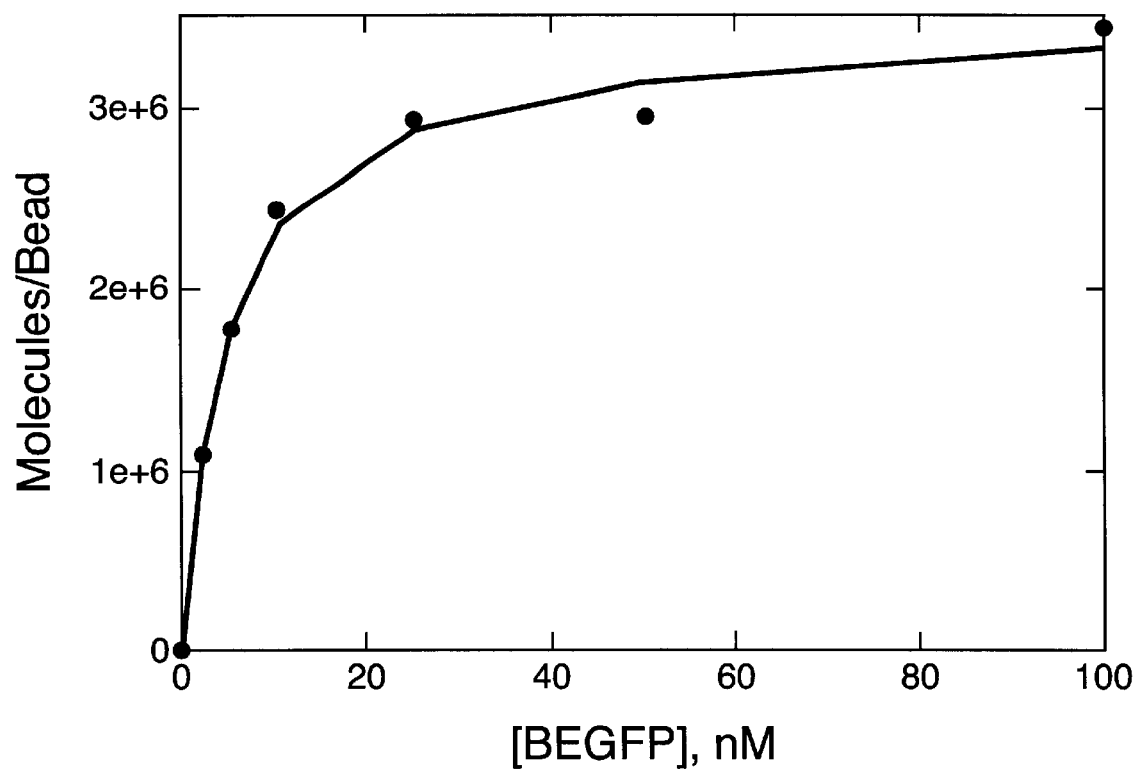
FIG. 1 is a graph of the number of biotinylated enhanced green fluorescent protein molecules per bead as a function of the concentration of biotinylated enhanced green fluorescent protein when titrated onto 7.4 μm diameter avidin beads, as measured by flow cytometry.

Briefly, the present invention includes the generation of a GFP-based microsphere calibration standards for rendering quantitative the use of GFP fusion proteins in fluorescent protein applications. Affinity tags fused with fluorescent proteins are attached to binding partners incorporated onto microspheres, thereby affixing the fluorescent protein to the microspheres. Green fluorescent protein is first generated according to standard procedures, with slight modifications including the use of a growth medium supplemented with biotin to improve yield. Biotinylated GFP is formed as a result of this process. Biotinylated proteins are commonly made since they can readily be purified on avidin columns.

The biotin affinity tag is essential for immobilizing the GFP on the avidin beads of the present invention. For characterization by fluorimetry and flow cytometry, 7.4 µm avidin or avidin beads were incubated at various concentrations with the biotinylated GFP and washed to remove any unbound GFP. Avidin beads incubated with biotin showed no biotinylated GFP uptake indicating that the biotinylation is essential for the attachment of the GFP to the beads. Binding of biotinylated enhanced GFP (BEGFP) to the beads has been found to be stable with a $K_d$ of 4 nM, and saturates at about $3.0 \times 10^6$ biotinylated enhanced GFP molecules per bead.

Having generally described the present invention, the following EXAMPLE is intended to provide more specific details thereof.

EXAMPLE

A. Enhanced GFP (EGFP) Cloning, Expression and Purification

In order to construct an expression vector encoding a biotinylated S65T GFP mutant, the coding region from the pEGFP-N2 (Clontech, Palo Alto, Calif.; mutant specifics are described in the Clontech Living Colors literature) vector was subcloned in frame into the PinPoint Xa-1 vector (See, "PinPoint Protein Purification System," Promega Technical Manual V2020 (1993)), which carries a segment encoding a peptide which is biotinylated by the biotin holoenzyme synthetase (biotin ligase) in E. coli (See, "Biotination Of Proteins in vivo" by John E. Cronan, Jr., J. Biolog. Chem. 265, 10327 (1990)), using BamH I and Not I restriction endonucleases. Following the identification of a plasmid containing the gene encoding the biotinylated EGFP (BEGFP), BL21 (DE3) LysS Escherichia coli were transformed with the expression plasmid and grown overnight at 30° C. on a LB 50 µg/ml ampicillin, 20 µg/ml, chloramphenicol plate. A single colony was inoculated into 500 ml of LB broth supplemented with 50 µg/ml ampicillin, 20 µg/ml chloramphenicol, and 50 µM biotin and grown at 30° C. until reaching an optical density of 0.6–0.8 at 600 nm whereupon expression was induced with 1 µM IPTG and allowed to proceed overnight at 25° C.

The bacteria were recovered by centrifugation and lysed with two freeze-thaw cycles and sonication. The clarified lysate was then loaded onto a monomeric avidin resin pre-equilibrated in Dulbecco's Phosphate Buffered Saline (DPBS) supplemented with a general protease inhibitor solution diluted according to manufacturer's instruction. Following an overnight binding reaction at 4° C., the resin was washed in 80 column volumes of DPBS with protease inhibitors. Following elution in 5 mM biotin in DPBS, the eluate was dialysed against DPBS using a 12–14,000 D molecular weight cutoff dialysis membrane to remove free biotin. The protein content was checked by bicincochinic acid protein assay (BCA) absorbance at 280 nm using an extinction coefficient of 21,290 $M^{-1}$ $cm^{-1}$ calculated from the amino acid sequence; and absorbance at 488 nm using the 61,000 $M^{-1}$ $cm^{-1}$ extinction coefficient of the EGFP fluorophore quoted in Clontech's Living Colors Literature, supra.

B. Spectroscopy

All EGFP emission scans were performed on a fluorescence spectrometer equipped with a 500 W Xenon lamp. The excitation wavelength was 488 or 470 nm, depending on the experiment. Emission was monitored from 500–650 nm, for excitation at 488 and 490–650 nm for excitation at 470 nm. Protein assays (BCA) (absorbance maxima at 562 nm) were read on a microplate reader using a 555 nm filter.

C. Flow Cytometry

Flow cytometry measurements were made using a fluorescence-activated cell sorter. For simultaneous fluorimetry and flow cytometry, 7.4–7.5 µm diameter avidin or streptavidin at $1 \times 10^6$ beads/ml were incubated for $\geq 30$ minutes with a range of BEGFP concentrations in phosphide buffered saline solution (DPBS)/0.1% bovine serum albumin (BSA) to give a reaction bead concentration of $1 \times 10^6$/ml. The beads were pelleted, washed in DPBS/0.1% BSA to remove unbound BEGFP and resuspended in the original volume. Emission scans were performed on the original supernatant, the wash, and the washed, resuspended beads. Samples containing beads were continuously mixed with a magnetic stirrer while in the fluorimeter. The same bead samples were transferred to a FACS (fluorescent activated cell sorter) tube containing an equal volume of DPBS and run on the flow cytometer. For samples measured only by flow cytometry, reactions were carried out in 0.5 ml with a final bead concentration of $1 \times 10^5$ to $1 \times 10^6$/ml, depending on the experiment. Both blocking and binding reactions were carried out for a minimum of 30 minutes at room temperature. Specific binding (i.e., BEGFP binding due to the biotin avidin link) was determined by subtracting nonspecific binding from total. Nonspecific binding was assessed by pre-blocking avidin sites with 50 µM biotin.

D. Expression and Purification of BEGFP

The S65T GFP mutant was selected over the wild type since, when compared to the wild type GFP, the S65T mutants have excitation and emission profiles more closely resembling the commonly used dye fluorescein. Therefore, Clontech's "enhanced" GFP was employed in the form of pEGFP-N2. The EGFP DNA coding sequence was extracted from this plasmid and inserted in frame into the PinPoint Xa-1 vector which carries a segment encoding a peptide which is biotinylated in E. coli. Next, the protein was expressed in bacteria and purified to homogeneity using affinity chromatography.

E. Characterization of Standards

Following successful expression of BEGFP, the protein was attached to the beads. First, it was necessary to ascertain the concentration of the purified BEGFP. To do so, three protein determination methods were compared: protein assay, absorbance at 280 nm using an extinction coefficient determined from the amino acid sequence, and absorbance at 488 nm using the extinction coefficient of the fluorophore. Each of these methods has its limitations. Variation within protein assays may be due to protein standard selection (bovine serum albumin vs. lysozyme, for example) and variation among protein assays due to differences in recognition moieties among the types of assays available.

For quantitative standards the following questions must be addressed: 1) Does the fluorescence of free BEGFP differ from that of the bound; 2) How much GFP is bound to the bead; and 3) How stable is the BEGFP-immobilized avidin interaction?

An equilibrium titration of nM quantities of BEGFP onto avidin beads at $1 \times 10^5$ beads/ml in the presence of 0.1% BSA was performed. The fluorescence of the supernatant was measured by fluorimetry and that of the beads using fluorimetry and FC. In order to assess the specificity of the BEGFP-immobilized avidin interaction, an equilibrium binding experiment was conducted in the presence of 0.1% BSA (to reduce nonspecific binding) where the avidin sites were preblocked using 50 µM biotin. The results of these titrations are shown in FIG. 1.

Whether the binding of BEGFP to the bead caused a change in fluorescence as compared to free BEGFP was next investigated. The same concentration of free BEGFP and avidin bead bound BEGFP were compared in the cuvette. The results indicate that no change of fluorescence intensity with attachment to the microspheres.

Figure 2:
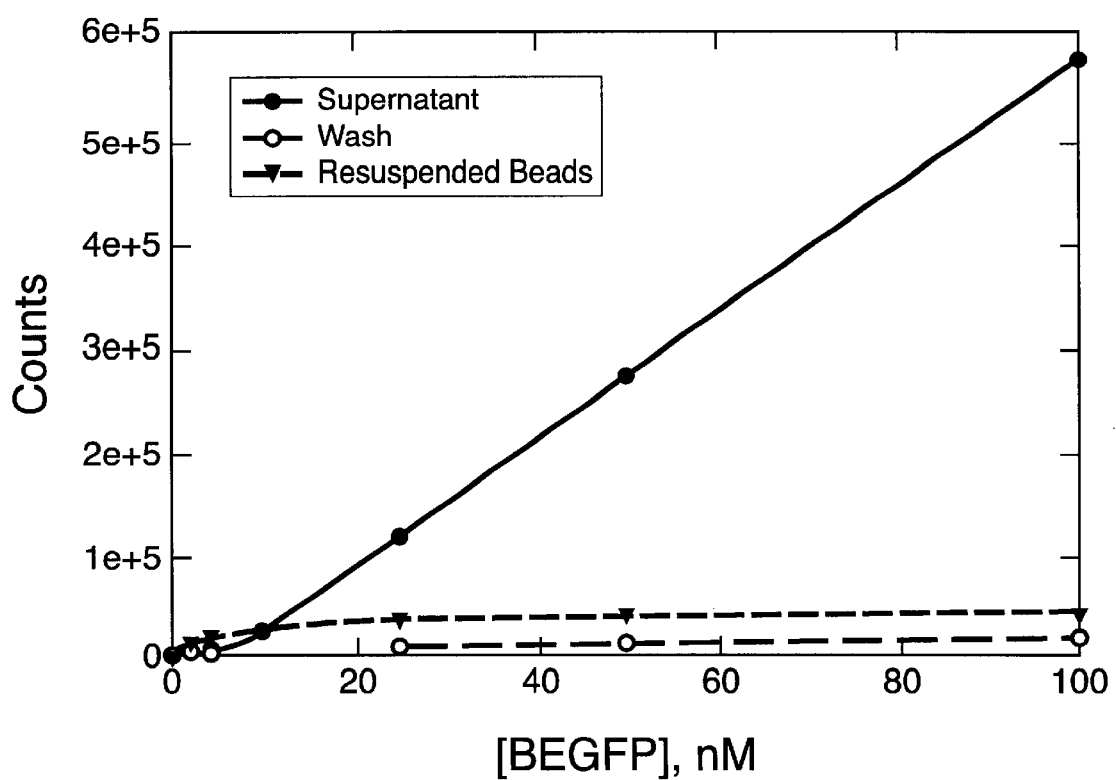
FIG. 2 is a graph of the fluorimetry signal intensity for biotinylated enhanced green fluorescent protein as a function of the concentration thereof when titrated onto 7.4 μm diameter avidin flow cytometer beads for resuspended beads (solid inverted triangles), for the supernatant solution used to prepare the fluorescent bead standards (solid circles), and for the wash solution (open circles).

FIG. 2 is a graph of the fluorimetry signal intensity for biotinylated enhanced green fluorescent protein as a function of the concentration thereof when titrated onto 7.4 $\mu$m diameter avidin beads for resuspended beads (solid inverted triangles), the original supernatant solution (solid circles), and for the wash solution (open circles). Results were derived from integrated peak emission from washed beads resuspended in DPBS. The BEGFP is first mixed with the microspheres at chosen concentrations, which are then washed and resuspended. It is clear from the curves in the graph that the BEGFP is not easily removed from the beads, once attached thereto, and that the concentration of BEGFP on the beads saturates.

Figure 3:
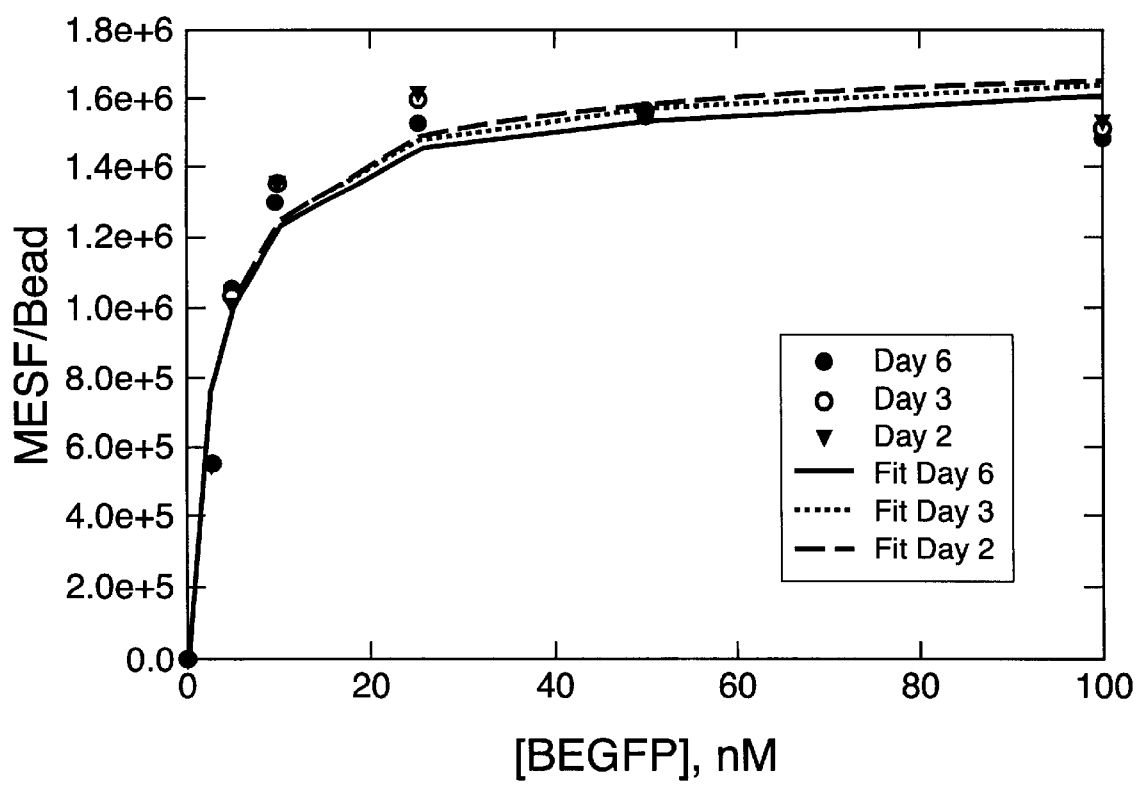
FIG. 3 is a graph of the fluorescence from biotinylated enhanced green fluorescent protein for each bead pre-bound therewith in a flow cytometer as a function of the concentration of biotinylated green fluorescent protein in the titration solutions, used to prepare the bead standards, when the beads are exposed to a biotin solution for various time periods, and shows the stability of biotinylated enhanced green fluorescent protein immobilized on streptavidin.

The question of stability of the BEGFP-avidin interaction was addressed in two ways. A batch of beads was prepared and, using FC, the change in fluorescence was measured over a week's time. Second, a biotin competition experiment was performed where biotin was added to prebound BEGFP avidin beads and the decrease in fluorescence measured over time by FC. FIG. 3 illustrates the results of these experiments.

The foregoing description of the invention has been presented for purposes of illustration and description and is not intended to be exhaustive or to limit the invention to the precise form disclosed, and obviously many modifications and variations are possible in light of the above teaching. For example, the approach to making fluorescent protein standards of the present invention can be extended by employing other attachment schemes such as histidine-tagged GFP attached to metal beads and a glutathione S-transferase-GFP bound to glutathione beads, as two examples. Additionally, the development of other suitable fluorescent proteins which could be similarly affinity labeled, purified and attached to microspheres would also increase the number of standards. A recently characterized class of red and orange emitting fluorescent proteins termed phytofluors has recently been reported. See, e.g., "The Phytofluors: A New Class Of Fluorescent Protein Probes" by J. T. Murphy and J. C. Lagarias, Current Biology 7, 870 (1997).

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for the preparation of recombinant fluorescent protein standard microspheres suitable for flow cytometry, which comprises the steps of:

(a) fusing an affinity tag with the recombinant fluorescent protein;

(b) mixing a first chosen quantity of said recombinant fluorescent protein/affinity tag fusion with a second chosen quantity of microspheres onto which a binding partner for said affinity tag is attached, whereby the recombinant fluorescent protein is immobilized on the microspheres; and (c) quantitatively observing the fluorescence from the microspheres at a chosen wavelength in a flow cytometer such that the calibration of the quantity of recombinant fluorescent protein thereon is obtained.

2. The method as described in claim 1, wherein the recombinant fluorescent protein is enhanced green fluorescent protein wherein the affinity tag is biotin, and wherein the binding partner is avidin.

3. The method as described in claim 2, wherein the microspheres are avidin microspheres.

4. The method as described in claim 1, wherein the recombinant fluorescent protein is enhanced green fluorescent protein, wherein the affinity tag is biotin, and wherein the binding partner is streptavidin.

5. The method as described in claim 4, wherein the microspheres are streptavidin microspheres.

6. The method as described in claim 1, wherein the recombinant fluorescent protein is enhanced green fluorescent protein, wherein the affinity tag is histidine, and wherein the binding partner is a metal ion.

7. The method as described in claim 6, wherein microspheres are metal microspheres.

8. The method as described in claim 1, wherein the recombinant fluorescent protein is enhanced green fluorescent protein, wherein the affinity tag is S-transferase, and wherein the binding partner is glutathione.

9. The method as described in claim 8, wherein the microspheres are glutathione microspheres.

10. The method as described in claim 1, wherein fluorescence from a suspension of the recombinant fluorescent protein standard microspheres is compared with the fluorescence from a solution containing a known quantity of the fluorescent protein in order to establish a calibration curve for the recombinant fluorescent protein standard microspheres.

* * * * *